United States Patent [19]

Köll

[11] Patent Number: 4,863,890

[45] Date of Patent: Sep. 5, 1989

[54] PROCESS FOR PREPARING A RUTHENIUM-PROMOTED, HALOGEN-CONTAINING NICKEL AND/OR COBALT CATALYST AND A CATALYST PREPARED BY THE PROCESS

[75] Inventor: Juhan Köll, Stenungsund, Sweden

[73] Assignee: Berol Kemi AB, Stenungsund, Sweden

[21] Appl. No.: 63,530

[22] Filed: Jun. 18, 1987

Related U.S. Application Data

[63] Continuation-in-part of Ser. No. 647,471, Sep. 5, 1984, Pat. No. 4,701,434.

[30] Foreign Application Priority Data

Sep. 9, 1983 [SE] Sweden ............................ 83048280
Jul. 11, 1986 [SE] Sweden ............................ 86030889

[51] Int. Cl.$^4$ ...................... B01J 27/28; B01J 27/13
[52] U.S. Cl. .................................................. 502/230
[58] Field of Search ............... 502/230, 259, 260, 326, 502/327

[56] References Cited

U.S. PATENT DOCUMENTS

| 1,449,423 | 3/1923 | Lowy et al. ...................... 564/402 |
| 2,365,721 | 12/1944 | Olin et al. ........................ 260/585 |
| 2,666,756 | 1/1954 | Boyd et al. ................... 502/326 X |
| 3,278,598 | 10/1966 | Markiewitz ..................... 260/563 |
| 3,595,932 | 7/1971 | Maslyansky et al. ............ 260/672 |
| 3,766,184 | 10/1973 | Johansson et al. .............. 260/268 |
| 3,896,173 | 7/1975 | Drake ......................... 260/583 P |
| 4,097,368 | 6/1978 | Hayes ............................ 208/139 |
| 4,115,463 | 9/1978 | Murtha ...................... 502/230 X |
| 4,263,175 | 4/1981 | Pesa et al. ...................... 502/326 |
| 4,268,699 | 5/1981 | Murtha et al. .................. 585/268 |
| 4,510,320 | 4/1985 | Pesa et al. .................. 502/326 X |

FOREIGN PATENT DOCUMENTS

| 721732 | 11/1965 | Canada ............................. 502/326 |
| 0030434 | 6/1981 | European Pat. Off. ........... 502/326 |
| 0055512 | 10/1981 | European Pat. Off. . |
| 0053819 | 6/1982 | European Pat. Off. . |
| 48-66086 | 2/1973 | Japan ............................. 502/326 |
| 49-119887 | 8/1974 | Japan ............................. 502/326 |
| 0123847 | 7/1968 | Norway . |
| 1604246 | 12/1981 | United Kingdom . |

*Primary Examiner*—W. J. Shine
*Attorney, Agent, or Firm*—Spencer & Frank

[57] ABSTRACT

Process for preparing a ruthenium promoted, halogen-containing, nickel and/or cobalt catalyst includes impregnating, in one or more steps, a porous metal oxide support with a nickel compound and/or a cobalt compound, and a ruthenium compound to form a catalyst intermediate; reducing the nickel compound and/or cobalt compound, and ruthenium compound, in one or more steps, to the respective metal by reacting the catalyst intermediate with hydrogen gas at an elevated temperature sufficient to reduce the respective compounds to the metal; and introducing halogen by adding a halide compound at any stage in the process. Catalyst prepared by the above process and use thereof.

36 Claims, No Drawings

PROCESS FOR PREPARING A RUTHENIUM-PROMOTED, HALOGEN-CONTAINING NICKEL AND/OR COBALT CATALYST AND A CATALYST PREPARED BY THE PROCESS

This application is a continuation-in-art application of Ser. No. 647,471, filed Sept. 5, 1984, now U.S. Pat. No. 4,701,434, and is related to Ser. No. 940,221, filed Dec. 8, 1986, which is a divisional application of Ser. No. 647,471, now U.S. Pat. No. 4,701,434.

BACKGROUND OF THE INVENTION

1. Field of the Invention

This invention relates to a process for preparing a ruthenium-promoted, nickel and/or cobalt catalyst, and to a catalyst prepared by the process. Such catalysts are useful as dehydrogenation-hydrogenation catalysts and are particularly useful for the amination of alkylene oxides, hydroxyl-containing compounds, such as alcohols, phenols and alkanolamines, aldehydes and ketones.

2. Background of the Art

Catalytic amination of alcohols is a well-known process. By this process alkylene oxides, hydroxyl-containing compounds, aldehydes, and ketones can be aminated by reacting the compounds with ammonia, primary amines or secondary amines in a continuous or batchwise process in the presence of hydrogen gas and a hydrogenation-dehydrogenation catalyst. All hydrogen atoms on an ammonium or amine nitrogen are potentially replaceable by the alkyl radical of the alkylene oxide, hydroxyl-containing compound, aldehyde and ketone, so that the reaction product will be a mixture of primary, secondary, and tertiary amines.

When aminating hydroxyl-containing compounds, such as ethylene glycols and ethanolamines, not only straight-chain di- and polyamines, but also branched chain polyamines and six-membered heterocyclic amines, such as piperazine, morpholine, and their derivates, are obtained. The most desirable products in the manufacture of ethylene amines are those containing mainly primary amino groups. Ethylene amines containing tertiary amino groups and heterocyclic rings are of less commercial interest.

Various catalysts have been used to catalyze the process and most of then are based on nickel and/or cobalt. In order to improve the selectivity in respect to the product mix and to increase the reaction rate, a large number of promotors have been used, such as compounds of copper, magnesium, chromium, iron, and zinc. Patents describing amination of organic substances include U.S. Pat. No. 1,449,423 to Lowy et al and U.S. Pat. No. 2,365,721 to Olin et al.

U.S. Pat. No. 3,766,184 to Johansson et al discloses a nickel and/or cobalt and iron-containing catalyst which increases the formation of ethylene diamine and decreases the formation of piperazine. In U.S. Pat. No. 3,278,598 to Markiewitz, a Raney nickel catalyst is described in which rodium, palladium, or ruthenium supported on carbon is introduced as a co-catalyst. However, this catalyst increases the formation of secondary amines at the expense of primary amines.

U.S. Pat. No. 4,115,463 to Murtha discloses a catalyst for conversion of aromatic hydrocarbons to cycloalkylaromatic hydrocarbons. The catalyst consists essentially of from 0.01 to 0.3 wt % ruthenium, from 0.03 to 1.0 wt % nickel, and a support material. The catalyst is prepared by a process in which ruthenium and nickel are applied to the support material, such as active clay or synthetic silica-alumina, as alcholic or aqueous solutions of a ruthenium halide salt and a nickel halide salt. Following impregnation, the catalytic composite is dried under conditions sufficient to remove solvent, but insufficient to calcine the catalyst composition. In the conversion, monocyclic aromatic hydrocarbons are contacted by the catalyst in the presence of hydrogen at a temperature ranging from 100° to 275° C. Prior to contacting the feedstock, the catalyst may be treated by flowing hydrogen over the catalyst for 0.1 to 10 hours at 100° to 275° C. In the finished catalyst, however, the nickel continues to be present as the nickel halide salt.

In U.S. Pat. No. 4,510,320 to Pesa et al, a catalyst is disclosed for producing aliphatic carboxylic esters from acetic acid and synthesis gas. The catalyst contains mixed oxides of ruthenium, nickel, an alkali metal selected from Na, Li, K, Rb and Cs, and optionally a promotor metal oxide selected from Co, Cd, Zn, or mixtures thereof. The catalyst may be prepared by conventional methods including mixing components with a liquid, filtering, drying, calcining, such as for 3 hours at 350° C. in air, and grinding, followed by coating upon a support, such as an alumina-silica support. Preferably the catalyst is utilized in a partially reduced state, for example, with hydrogen gas at 500° C. for 2 hours, but the catalyst is not totally reduced to the metallic state and thus retains its oxide character.

SUMMARY OF THE INVENTION

It is an object of the present invention to provide a catalyst which is useful as a hydrogenation-dehydrogenation catalyst and favors the formation of primary and noncyclic amines when used in amination reactions.

It is a further object of the present invention to provide a process for preparing the above catalyst.

In accordance with the present invention a new catalyst has been found which is useful as a hydrogenation-dehydrogenation catalyst and favors the formation of primary and noncyclic amines when used in amination reactions. The catalyst is a supported nickel and/or cobalt catalyst containing halogen and promoted with ruthenium in which the metals are present in the metallic state. It contains, calculated on an oxide-free, i.e., metallic, basis and in weight percent based on the total weight of the catalyst, from 4 to 40 wt. % of at least one metal selected from nickel and cobalt, and from 0.1 to 5 wt. % ruthenium on a porous metal oxide support. Preferably, the catalyst contains from 0.1 to 5 wt. % halogen and the porous metal oxide support is comprised of at least 50% by weight of a material selected from activated alumina and silica.

Thus the present invention provides a ruthenium-promoted, halogen-containing, nickel and/or cobalt catalyst containing, based on the total weight of the catalyst, from 4 to 40% by weight of at least one metal selected from nickel and cobalt; from 0.1 to 5% weight of ruthenium; from 0.1 to 5% by weight of halogen; and a porous metal oxide support comprised of at least 50% by weight of a material selected from activated alumina and activated silica, prepared by a process including the steps of impregnating the porous metal oxide support with a solution or slurry of at least one metallic compound selected from a nickel compound and a cobalt compound to provide a first catalyst intermediate; decomposing the at least one metallic compound of the first catalyst intermediate into metals or oxides under conditions of temperature and pressure effective to cause such decomposition and to provide a second catalyst intermediate containing one or more of at least one metal selected from nickel and cobalt, and at least one metal oxide selected from nickel oxide and cobalt oxide; impregnating the second catalyst intermediate with a solution or slurry of a ruthenium compound to provide a third catalyst intermediate; reducing the ruthenium compound of the third catalyst intermediate into ruthenium metal by causing the ruthenium compound to react with hydrogen gas at an elevated temperature sufficient to reduce the ruthenium compound to ruthenium metal; reducing the at least one metal oxide selected from nickel oxide and cobalt oxide to metal by causing the at least one metal oxide to react with hydrogen gas at an elevated temperature sufficient to reduce the at least one metal oxide to at least one metal selected from nickel and cobalt; and introducing halogen into the catalyst by adding a halide compound as a liquid, gas or in solution at any stage of the process, wherein the halide compound is any halide compound except a ruthenium halide compound.

It has now been found that the advantageous properties of this catalyst seem to be related to the presence of halogen in it and that this catalyst can be obtained by introducing halide compound into the catalyst at any any stage of a process for its manufacture.

The present process for preparation of a ruthenium promoted, nickel and/or cobalt catalyst includes impregnating a porous metal oxide support in one or more steps with a nickel and/or cobalt compound and a ruthenium compound; reducing the nickel and/or cobalt compound and the ruthenium compound into finely divided nickel and/or cobalt and ruthenium metals; and introducing halogen into the catalyst by adding at least one halide compound at any stage of the process.

The halide compound may be a ruthenium halide compound, in which case the halide compound is added during impregnation with ruthenium. Preferably, the halide compound is not a halide of nickel or cobalt for reasons to be discussed in the following. According to one embodiment, the halide compound is added in any form other than as a halide of nickel, cobalt or ruthenium.

According to one preferred embodiment of the process, the catalyst may be prepared by first preparing by any conventional method a catalyst intermediate consisting of nickel and/or cobalt as finely divided metals or oxides on a porous metal oxide support; then treating the thus prepared catalyst intermediate with halide compound; thereafter impregnating the halide-treated catalyst intermediate with a soluble ruthenium compound; and finally reducing the ruthenium compound, and any nickel and/or cobalt remaining as oxides into corresponding finely divided metals.

Another preferred embodiment is a combined impregnation in which the support is impregnated with nickel and/or cobalt compound, ruthenium compound, and halide compound from one solution containing all three constituents. The impregnation step is followed by calcination and reduction steps, which transfer all nickel and/or cobalt, and ruthenium compounds into finely distributed metals.

The treatment with halide compound may be performed at any step in the catalyst preparation procedure, including:

(a) introducing halide compound prior to addition of the nickel and/or cobalt compound to the metal oxide support;
(b) impregnating the support with a mixture of nickel and/or cobalt compound and halide compound;
(c) decomposing the supported nickel and/or cobalt compound into metal or oxide in an atmosphere containing a suitable halide compound;
(d) treating the catalyst intermediate comprising supported nickel and/or cobalt metal or oxide with halide compound;
(e) adding halide compound to the ruthenium compound solution used for impregnation of the catalyst intermediate;
(f) treating the catalyst intermediate containing supported nickel and/or cobalt metal or oxide and ruthenium metal with halide compound before the final reduction step in which all the metals are reduced to the metallic state;
(g) adding volatile halide compound to the hydrogen gas employed during a reduction step; and
(h) adding halide compound to the impregnation solution containing nickel and/or cobalt compound and ruthenium compound in a combined impregnation step.

The halide compound can be used as a gas or liquid, in solution in water or other suitable solvent, or dissolved and/or slurried together with one or more of the catalyst ingredients in a suitable solvent or liquid medium.

The choice of halide compound type and amount, treatment temperature, pressure, and duration, and treatment method depends on the support material and shape, available catalyst preparation equipment, ruthenium compound used, and availability of different halide compounds. The optimal parameters may vary from different applications for which the catalyst is to be used and therefore cannot be given, but must be determined individually for each combination of variables. It is generally advisable to treat with an excess of the halide compound to insure incorporation of the desired amount of halogens in the finished catalyst. For example, some halogen is lost as hydrogen halide gas during the reduction steps, however, so long as process temperatures are kept below about 600° C., halogen loss is not appreciable.

In a preferred embodiment, the halide compound may be any halide compound except a ruthenium halide compound. Alternately, in another preferred embodiment, the halide compound may be any halide compound except a nickel halide compound or a cobalt halide compound and/or except a ruthenium halide compound.

The catalyst, produced in accordance with the present process exhibit excellent hydrogenation and/or dehydrogenation properties. They can be used advantageously in amination reactions in which hydroxyl containing compounds, such as alcohols, phenols and alkanolamines, aldehydes, ketones, and alkylene oxides are reacted with ammonia, primary amines, or secondary amines. Higher yields of the desired primary amines and polyamines are obtained, and the formation of undesired by-products is largely reduced as compared to amination carried out in the presence of a prior art catalyst.

DESCRIPTION OF THE PREFERRED EMBODIMENTS

Numerous tests have shown that halide amounts (calculated as weight percent of elemental halogen in the final catalyst) between about 0.1 and about 5 percent are generally preferred. Most preferred amounts are from 0.25 to 2.5 percent. The addition of halide compound and introduction of halide ion into the catalyst should preferably be performed in such a way that the above-mentioned halogen amounts are obtained in the finished catalyst.

Primarily preferred halide compounds are hydrogen halides, such as hydrofluoric acid, hydrochloric acid, hydrobromic acid and hydroiodic acid. Other preferred halide compounds are halide salts of weak bases which provide hydrogen halides at elevated temperatures. Examples of such compounds include ammonium fluoride, ammonium acid fluoride, ammonium chloride, ammonium bromide, and ammonium iodide. Further suitable halide compounds are neutral or acid salts of hydrohalide acids that form hydrogen halides when exposed to acidic gases or liquids present or liberated during the catalyst preparation. Examples of such compounds include alkali metal halides, and alkaline earth metal halides. Suitable halide compounds also comprise organic halogen compounds which can decompose into hydrogen halides. Examples of useful organic halogen compounds include organic acid chlorides and chlorinated hydrocarbons and their derivatives, such as acetyl chloride, tertiary butyl chloride and chloroacetic acids. Finally, inorganic compounds that will decompose into acidic halides may be used, such as sulphuryl chloride and thionyl chloride. The term "halide compound" as used herein therefore includes all of the above types of halogen-containing compounds.

According to the invention, any conventional metal oxide support containing at least 50% by weight of alumina and/or silica may be used. The metal oxide support materials which have been found to produce the most active and most selective amination catalysts are those containing more than 95% activated alumina. The preferred porous metal oxide support therefore contains at least 50 percent, most preferably about 95 percent, activated alumina. Examples of such supports are those consisting of alumina/silica, alumina/titania, alumina//magnesia, alumina/zirconia, and other combinations. The inner surface area of the catalyst support is not critical and may vary from 10 to 1,000, preferably 20-400 square meters per gram of support, but the area is suitably adapted to the metal amount in order to achieve primarily a monomolecular layer of catalyst metals on the support. A number of such support materials are wellknown in the art and are also commercially available.

The chemical nature of the support materials exerts a large influence on the catalyst's properties. As an example, carbon-supported, ruthenium-promoted, nickel and/or cobalt catalysts show no selectivity for primary amines, but on the contrary promote formation of secondary and tertiary amines. Other supports having a primarily acid nature may give better activity with ruthenium promotion than without, but the catalysts made from these supports are less selective than those constituted of metal oxides.

The support material used in the invention may be coprecipitated with nickel and/or cobalt salts, or impregnated with solutions of these metal salts. Various organic and inorganic nickel and cobalt salts may be used for coprecipitation or impregnation. Examples of suitable salts are nickel nitrate, nickel acetate, nickel formate, and nickel acetonyl acetate as well as corresponding cobalt salts. Nickel and/or cobalt halides are nor preferred. Nickel chloride and/or cobalt chloride may be used, but these salts are not decomposed by heating in air. However, they can be converted to metal by heating in hydrogen gas. Another method of depositing metals on the support is using nickel or cobalt carbonyl gas and decomposing it on the surface of the support as a deposit of extremely finely divided metal.

In accordance with the invention, nickel and cobalt may be used alone, in admixture with each other, or layered one on top of the other. Which metal and which application method will give the best result in a particular amination process cannot be predicted, but must be determined experimentally. As long as recognized principles of hydrogenation catalyst manufacture are used, the particular method of impregnating or coating the nickel and/or cobalt metal onto the support material has not been found to have any significant effect on the activity or selectivity of the final catalyst.

The amount of nickel and/or cobalt to be used depends on the composition and physical characteristics such as surface area and pore distribution of the catalyst support. In most cases, the most active catalysts have been found to be those in which the content of nickel and/or cobalt ranges from 5 to 20 percent by weight, based on the total weight of the catalyst, and the content of ruthenium ranges from 0.2 to 3 percent by weight, based on the total weight of the catalyst, provided on a support having an inner surface area ranging from 50 to 150 square meters per gram. The amount of nickel and/or cobalt metal provided on the support effects the activity of the catalyst, but not its selectively.

In one embodiment of the invention, the support material is impregnated with the desired amount of nickel and/or cobalt salt, is dried and then calcined to decompose the salts into metal oxides to form a catalyst intermediate. This can be accomplished by heating the catalyst first gently and, if desired, under reduced pressure to evaporate the impregnation solvent, followed by raising the temperature to 300°–600° C. in a stream of air, but above the decomposition temperature of the salt(s) used, and maintaining that temperature until the salt(s) are completely transformed into oxides. It is also possible to transfer the oxides formed into metals prior to ruthenium impregnation by reacting such a catalyst intermediate with hydrogen gas at elevated temperature. It is essential, however, that the remainance of soluble salts, especially of nitrates, is minimized. The nitrates may react with, and decompose the halogen in the catalyst thus inactivating it. Nitrates may dissolve in the reaction mixture when the catalyst is used for hydrogenation/dehydrogenation and catalyze possible side reactions. The salts may also form a support for catalytic metals, which are removed from the catalyst when the salt dissolves.

As the ruthenium compound, ruthenium compounds can be used which are soluble in water, organic solvents or volatile acids, and transferable into metallic ruthenium, e.g., by reducing the ruthenium compound in hydrogen gas at an elevated temperature. Non-halide ruthenium compounds can be used, as well as ruthenium halides. The temperature for converting ruthenium compound into metallic ruthenium has to be chosen to suit to the particular ruthenium compound used, but normally those ruthenium compounds are chosen which are convertible to the metallic form at a temperature between 100° and 400° C. Most preferred non-halide ruthenium compounds, considering availability and price, are ruthenium nitrate and ruthenium nitrosyl nitrate.

According to one embodiment of the invention, the ruthenium treatment of the nickel oxide and/or cobalt oxide catalyst or the nickel and/or cobalt catalyst is performed by impregnating it with a solution in water or in an organic solvent of the chosen ruthenium compound to form a catalyst intermediate, followed by drying the catalyst at 50°-100° C. in a stream of inert gas, air or hydrogen. The impregnation may be performed by spraying the solution evenly onto the catalyst, adsorbing the ruthenium compound from a dilute solution onto the surface of the coated support, or wetting the catalyst with a ruthenium compound in solution, followed by evaporating the solvent. To prevent hydrolysis of the ruthenium compound, particularly if a ruthenium salt, the impregnating solution may contain minor amounts of hydrochloric acid or another hydrogen halide.

The ruthenium compound is then reduced to ruthenium metal by heating the impregnated catalyst intermediate at about 150° to 200° C. for from 0.5 to 3 hours in a stream of hydrogen gas. Then, in order to reduce any remaining nickel and/or cobalt oxides into finely divided metal, the temperature is raised, preferably to 300° to 600° C., while still in the stream of hydrogen, and the temperature is kept at that level until the desired degree of reduction is reached. Usually a high degree of reduction is preferred, but because of the possibility of sintering the support material and the nickel and/or cobalt powder upon prolonged heating, a lower degree of reduction is sometimes tolerated in order to avoid a reduction in surface area associated with sintering. In case cobalt and/or nickel is present in metallic form at the impregnation with ruthenium halide, only reduction of ruthenium is necessary and may be accomplished by heating at about 150° to 200° C. as before.

The activated catalyst is best handled in the absence of air in order to prevent the reoxidation of nickel and/or cobalt. The catalyst may also be stabilized by gentle oxidation, carbon dioxide treatment, or other conventional techniques for stabilizing pyrophoric catalyst, and may then be handled in air prior to its utilization.

Various ruthenium halides can be used in the ruthenium treatment step according to this invention. Examples of suitable salts include soluble forms of ruthenium trichloride, ruthenium ammonium chloride, ruthenium potassium chloride, ruthenium nitrosyl chloride, ruthenium potassium nitrosyl chloride, chlororuthenous acid, ruthenium red (hydroxochlorotetramine ruthenium chloride), and corresponding bromides and iodides. The preferred ruthenium halide compound, considering availability, price, and performance, is ruthenium trichloride hydrate. Non-halides, such as ruthenium dioxide, ruthenium sulphate, ruthenium nitrate, ruthenium nitrosyl nitrate, ruthenium ammonium nitrate, ruthenium acetyl acetonate, and potassium perruthenate, promote the activity of a nickel and/or cobalt catalyst, but do not give a noticeable improvement of the selectivity in organic hydrogenations, compared with corresponding catalysts without ruthenium promotion, unless utilized together with a halide compound in accordance with the invention.

The ruthenium-promoted, nickel/cobalt catalysts of the present invention may be further improved by incorporating certain additional components therein. Examples of such additional components are metals and metal oxides selected from among antimony, bismuth, cerium, chromium, copper, iron, manganese, molybdenum, rhenium, thorium, titanium, tungsten, uranium, vanadium, zirconium, and noble metals other than ruthenium. Other examples include compounds of phosphorus and boron.

As mentioned, the catalyst in accordance with the invention is especially suitable to be used in amination reactions. In an amination process, alkylene oxide, hydroxyl containing compounds, such as alcohols, phenols, and alkanolamines, as well as aldehydes and ketones, can be transferred into corresponding amines by reacting the compound with at least one of ammonia, primary amines or secondary amines in a continuous or batchwise process.

All hydrogen atoms on an amine nitrogen are potentially replaceable by the alkyl radical of the reacting alkylene oxide, hydroxyl or carbonyl compound, so the reaction product will be a mixture of primary, secondary, and tertiary amines. When aminating ethylene compounds, such as ethylene glycols and ethanolamines, cyclization occurs giving not only straight chain and branched di- and polyamines but also six membered heterocyclic amines, such as piperazine, morpholine, and their derivatives.

The most desirable products in the manufacture of ethylene amines are those containing mainly primary amino groups. By-products containing tertiary amino groups and heterocyclic rings are of less commercial value. The present catalyst has a surprisingly high selectivity for formation of primary and non-cyclic compounds at high reaction rate.

The amination of ethylene glycol with ammonia may be illustrated by chemical reactions (1) and (2) which include side reactions (3) and (4) and which describe a few of all possible reactions:

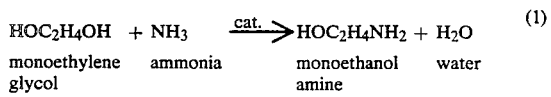

$$HOC_2H_4OH + NH_3 \xrightarrow{cat.} HOC_2H_4NH_2 + H_2O \quad (1)$$
monoethylene glycol / ammonia / monoethanol amine / water

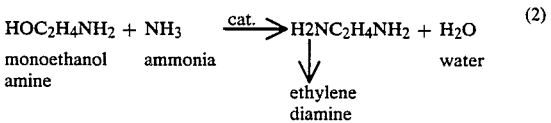

$$HOC_2H_4NH_2 + NH_3 \xrightarrow{cat.} H_2NC_2H_4NH_2 + H_2O \quad (2)$$
monoethanol amine / ammonia / ethylene diamine / water

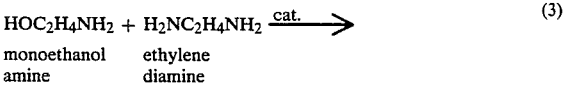

$$HOC_2H_4NH_2 + H_2NC_2H_4NH_2 \xrightarrow{cat.} \quad (3)$$
monoethanol amine / ethylene diamine $$H_2NC_2H_4NHC_2H_4NH_2 + H_2O$$
diethylene triamine / water

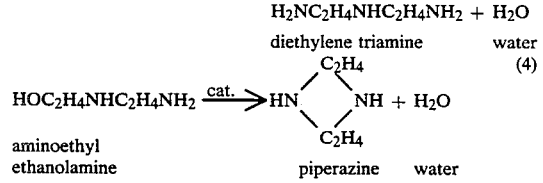

$$HOC_2H_4NHC_2H_4NH_2 \xrightarrow{cat.} HN\underset{C_2H_4}{\overset{C_2H_4}{\diagup\diagdown}}NH + H_2O \quad (4)$$
aminoethyl ethanolamine / piperazine / water Reactions (1) and (2) above consist of three consecutive steps:
(a) Dehydrogenating the hydroxyl containing compound to a corresponding aldehyde or ketone;

(b) Adding an aminating agent to that reaction product to form an imine; and (c) Hydrogenating the imine to the corresponding amine.

Consequently, the catalytic ability of the catalyst of this invention is also useful for amination of aldehydes and ketones and for hydrogenation of imines to the corresponding amines.

Alkylene oxides suitable for amination are those having from 2–22 carbon atoms in the alkylene group. Specific examples are ethylene oxide, 1,2-propylene oxide, 1,2-butylene oxide and 2,3-butylene oxide. Aliphatic alcohols which can be aminated in the process of the present invention include saturated aliphatic monohydric and polyhydric alcohols having from 1–30 carbon atoms, including, for example, saturated monohydric alcohols, such as methanol, ethanol, propanol, isopropanol, n-butanol, sec-butanol, tert-butanol, isobutanol, n-pentanol, isopentanol, neopentanol, n-hexanol, isohexanol, 2-ethyl hexanol, cyclohexanol, n-heptanol, n-octanol, 2-octanol, isooctanol, and tert-octanol, and various isomers of nonanol, decanol, hendecanol, dodecanol, tridecanol, tetradecanol, hexadecanol, and octadecanol, arachidyl alcohol, aliphatic dihydric alcohols having from 2–30 carbon atoms, such as ethylene glycol, diethylene glycol, triethylene glycol, tetraethylene glycol, and higher polyethylene glycols, 1,2- and 1,3-propylene glycol, dipropylene glycol, tripropylene glycol and higher polypropylene glycols, 1,2-butylene glycol, 1,3-butylene glycol, 1,4-butylene glycol, 2,3-butylene glycol, dibutylene glycol, tributylene glycol or higher polybutylene glycols, isomers of pentanediol, hexanediol, octanediol, nonanediol, decanediol, undecanediol, dodecanediol, tridecanediol, tetradecanediol, pentadecanediol, hexadecanediol, octadecanediol, eicosanediol, and trihydric and higher polyols having from 3–30 carbon atoms, such as glycerol, erythritol, pentaerythritol, sorbitol, mannitol, trimethylol ethane, trimethylol propane, heptanetriol, and decanetriol.

Further, it is possible to use aldehydes and ketones derived from the above mentioned alcohols, e.g., by dehydrogenation. Suitable aldehydes are formaldehyde, acetaldehyde, propionaldehyde, butyraldehydes, cyclohexanal, benzaldehyde, and aldehydes prepared by the dehydrogenation of dihydric and trihydric alcohols, monoalkylene glycol ethers, polyalkylene glycol ethers, and alkanolamines. Suitable ketones are acetone, methyl ethyl ketone, various isomers of pentanone and hexanone, 1-phenyl-2-propanone, acetophenone, n-butyrophenone, and benzophenone, as well as ketones prepared by dehydrogenation of dihydric and trihydric alcohols, mono- and polyalkylene glycol ethers and alkanolamines.

Among phenols suitable for amination may be mentioned phenol, o-cresol, m-cresol, p-cresol, pyrocatechin, resorcinol, hydroquinone and isomers of xylenol, and among aliphatic aminoalcohols those having from 2–30 carbon atoms, such as monoethanolamine, diethanolamine, aminoethyl ethanolamine, propanolamines, butanolamines, pentanolamines, hexanolamines, heptanolamines, octanolamines, decanolamines, dodecanolamines, tetradecanolamines, hexadecanolamines, octadecanolamines, and eicosanolamines. In addition, mixtures of the above alcohols can be employed, for example, mixtures of ethylene glycol and monoethanolamine, or mixtures of alkanolamines which are obtained by reacting alkylene oxides with ammonia.

The aminating agents are ammonia, primary amines, or secondary amines. The amines generally have alkyl groups of 1–20 carbon atoms, cycloalkyl groups of 5–8 carbon atoms and aryl- or arylalkyl groups of 6–40 carbon atoms. Examples of suitable amines are methylamine, ethylamine, n-butylamine, isobutylamine, ethylenediamine, benzylamine, dimethylamine and diethylamine. The aminating agents, as well as the alkylene oxides and hydroxyl-containing compounds, aldehydes and ketones can be used alone or in combination with one another.

The reaction between the aminating agent and the compound to be aminated is carried out in the presence of hydrogen gas in order to ensure a good yield of the desired amine products. Generally, the quantity of hydrogen gas required is relatively small, and corresponds to a proportion of from about 0.1 to about 2 moles per mole hydroxyl. Higher proportions of hydrogen can be employed, but generally, however, without any noticeable benefit. The aminating agent, such as ammonia, should be present in excess in the mixture, for example, within the range from about 2 to about 30 moles aminating agent per mole of the compound to be aminated, and preferably within the range from about 5 to about 15 moles per mole. The amount of the catalyst is not critical, but normally it will be from 0.1 to 25%, preferably from 1 to 15%, by weight of the total amount of starting reactants in a batchwise process.

In carrying out the amination process, an elevated temperature should be employed. Temperatures within the range from about 120° to 300° C. are suitable. Particularly good yields and good selectivities are obtained employing temperatures within the range from about 175° to about 225° C.

The amination process is carried out at a relatively high pressure. The pressure employed is dependent upon the molar ratio of the reactants, the reaction temperature, the amount of hydrogen, and the kind of operation. Generally, the pressure should be high enough to keep most of the reactants in the liquid phase. The pressure is normally within the range from about 8 to about 40 MPa and preferably from 15 to about 30 MPa.

The equipment used in carrying out the amination process of this invention can be any conventional high temperature and pressure equipment adapted for batch or continuous operation. In a batch process, a pressure reactor vessel can be used, such as an autoclave equipped with an agitator and heating means. The process can be carried out as a continuous process wherein the reactants in gas and liquid phase are passed under pressure over a solid catalyst bed maintained at the desired reaction temperature. The catalyst can also be provided in a fluidized bed, or passed countercurrently to the reaction mixture. The reaction mixture is worked up by first separating ammonia and hydrogen and then separating the various products by fractional distillation.

The invention is further illustrated by, but not limited to, the following examples which use amination of monoethanolamine to ethyleneamines as a measure of catalyst efficiency.

The abbreviations used in the examples and in the tables are:

| EDA | = | Ethylenediamine |
| MEA | = | Monoethanolamine |
| PIP | = | Piperazine |

|  |  |  |
|---|---|---|
| DETA | = | Diethylenetriamine |
| AEP | = | Aminoethyl piperazine |
| AEEA | = | Aminoethyl ethanolamine |
| HEP | = | Hydroxyethyl piperazine |

"Conversion percent" is defined as the amount of the starting compound for amination consumed in the reaction as a percent of the amount originally charged.

EXAMPLE 1

Step A. Nickel impregnation.

A saturated aqueous nickel nitrate solution containing one part by weight of nickel, calculated as metal, was added to 9 parts by weight of a catalyst support consisting of 95 percent gamma alumina. The support was in the form of tablets with length and diameter of 3 mm and a total surface area of about 100 square meters per gram of support.

Excess water was evaporated in a vacuum at about 75° C., the tablets were dried, and the nickel nitrate was decomposed by heating in air at 500° C. to nickel oxide. This alumina support, coated with finely distributed nickel oxide was used as catalyst intermediate here and in Examples 2 to 6, and in comparative Example A.

Step B. Acid treatment.

To the catalyst intermediate was added twice its weight of 18 percent aqueous hydrochloric acid solution. After 30 minutes at room temperature the excess liquid was removed, the tablets were dried at 110° C. and cooled. Analysis of the tablets gave a chlorine content of 0.56 percent, calculated as element on total weight of catalyst intermediate.

Step C. Ruthenium impregnation

The tablets were impregnated using a two percent aqueous solution of ruthenium nitrosyl nitrate, containing 0.5 percent of ruthenium, calculated as metal and based on the weight of the alumina support used. The tablets were then dried at 100° C. in air.

Step D. Reduction with hydrogen gas.

The ruthenium-impregnated tablets were heated in a stream of hydrogen gas, first for one hour at about 180°-200° C., then for four hours at 400° C., in order to reduce the majority of nickel and ruthenium salts in the tablets to metals in finely dispersed form.

Step E. Catalyst testing.

A 300 ml autoclave, equipped with a stirrer and temperature control, was flushed with nitrogen gas. Eight grams of the catalyst to be tested, 25 grams of MEA, 3.5 grams of water, and 65 grams of liquid ammonia were charted into the autoclave. The autoclave was closed, and hydrogen gas was introduced to a pressure of 5.5 MPa. The contents of the autoclave were heated to 200° C. and kept at this temperature with continuous stirring until the completion of the test.

Samples were withdrawn from the autoclave during the reaction and analyzed using Gas-Liquid Chromatography. The conversion percent of MEA was calculated, as well as weight percents of products formed in the reaction. From these figures the ratios of primary, secondary, and tertiary amino groups to total amino groups in the products formed, given as mole percent, were calculated and reported.

The results obtained in Example 1 are reported in Table I, as well as the results obtained in comparative Examples A, B, and Examples 2-17 which follow.

COMPARATIVE EXAMPLE A

A catalyst was prepared as described in Example 1, but the hydrochloric acid treatment (Example 1, Step B) was omitted.

EXAMPLES 2-4

Three catalysts were prepared as described in Example 1, but hydrochloric acid was replaced by the same molar amount of hydrofluoric acid (Example 2), hydrobromic acid (Example 3), or hydroiodic acid (Example 4).

EXAMPLE 5

A catalyst was prepared as described in Example 1, but the 18 percent aqueous hydrochloric acid solution was replaced by the same weight of 25 percent aqueous ammonium chloride solution.

EXAMPLE 6

A catalyst was prepared as described in Example 1, but the 18 percent aqueous hydrochloric acid solution was replaced by the same weight of 10 percent aqueous sodium chloride solution.

EXAMPLES 7-11

Catalysts were prepared according to Example 1, but the hydrochloric acid treatment (Example 1, Step B) was performed at different stages of the catalyst preparation.

EXAMPLE 7

The same alumina support as used in Example 1, was first treated with hydrochloric acid in the same way as described in Example 1, Step B. Then this support was impregnated first with nickel as described in Example 1, Step A, then with ruthenium as described in Example 1, Step C, and reduced and tested as described in Example 1, Steps D and E.

EXAMPLE 8

A catalyst was prepared and tested as described in Example 1, but acid treatment (Example 1, Step B) was omitted and nickel impregnation (Example 1, Step A) was performed with nickel nitrate dissolved in the same amount of hydrochloric acid as given in Example 1, Step B, instead of with a saturated aqueous solution of nickel nitrate.

EXAMPLE 9

A catalyst was prepared as described in Example 1, but the acid treatment (Example 1, Step B) was omitted and ruthenium impregnation (Example 1, Step C) was performed with ruthenium nitrosyl nitrate dissolved in the same amount of hydrochloric acid as given in Example 1, Step B, instead of with a two percent aqueous solution of ruthenium nitrosyl nitrate.

EXAMPLE 10

A catalyst was prepared as described in Example 1, but acid treatment (Example 1, Step B) was omitted. After reduction at 400° C. (Example 1, Step D) the catalyst was treated with hydrochloric acid as described in Example 1, Step B, then reduced again (final reduction step) and tested as described in Example 1, Steps D and E, respectively.

EXAMPLE 11

A catalyst was prepared as described in Example 9, but ruthenium nitrosyl nitrate was replaced by the same molar amount of ruthenium chloride hydrate.

EXAMPLE 12

A catalyst was prepared and tested as described in Example 1, but a silica/alumina catalyst support containing 87% silicon dioxide and having a total surface area of 60 square meters per gram was used instead of alumina support.

EXAMPLE 13

A catalyst was prepared and tested as described in Example 1, but nickel nitrate was replaced by the same molar amount of cobaltous nitrate.

EXAMPLE 14

90 parts by weight of catalyst support, consisting of 95 percent gamma alumina in the form of tablets with length and diameter of 3 mm and a total surface area of about 100 square meters per gram support, were treated with hydrochloric acid as described in Example 1, Step B.

A saturated aqueous solution containing 10 parts by weight of nickel and 0.5 parts by weight of ruthenium, calculated as metals, but applied as metal nitrates, was added to said hydrochloric acid treated catalyst support. Water was evaporated in a vacuum at about 75° C., and the tablets were dried. This catalyst intermediate was then reduced and tested as described in Example 1, Steps D and E.

EXAMPLE 15

A catalyst was prepared and tested as described in Example 1, but acid treatment (Step B) was omitted, and the nickel impregnation step (Step A) was modified by bubbling the air, used for decomposing the nickel nitrate, through an 18 percent aqueous solution of hydrogen chloride.

EXAMPLE 16

A catalyst was prepared and tested as described in Example 1, but acid treatment (Step B) was omitted, and reduction with hydrogen (Step D) was performed with hydrogen gas bubbled through an 18 percent aqueous solution of hydrogen chloride.

EXAMPLE 17

89.5 parts by weight of a catalyst support, consisting of 99 percent gamma alumina in the form of tablets with length and diameter of 3 mm and a total surface area of about 80 square meters per gram support, were impregnated with an aqueous solution of nickel nitrate, ruthenium nitrosyl nitrate and hydrochloric acid. The solution contained 10 parts by weight of nickel and 0.5 parts by weight of ruthenium, both calculated as metal, but applied as metal salts, and 1.1 parts by weight of hydrogen chloride. Water was evaporated in a vacuum at about 80° C., and the tablets were dried.

This catalyst intermediate was then reduced with hydrogen gas as described in Example 1, Step D, and tested as described in Example, 1 Step E.

EXAMPLE 18

A concentrated aqueous metal nitrate solution containing the amount of metals given in TABLE II was added to 90 grams of activated alumina catalyst support in form of tablets with length and diameter of about 3 mm and a surface area of about 100 square meters per gram support. Excess of the liquid was evaporated in vacuum at about 75° C., the tablets were dried, and the nitrates were decomposed to the corresponding oxides by heating to 500° C. in a stream of dry air. After cooling, the tablets are impregnated with a two percent aqueous solution of the ruthenium compound, the compound and amount of ruthenium is stated in TABLE II, and dried at 100° C. in air.

The tablets were then heated in a stream of hydrogen gas, first for one hour at about 150°–200° C. to convert the ruthenium compound to ruthenium metal, then for four hours at 400° C. to reduce the metal oxides to metals in a finely dispersed form.

EXAMPLE 19

A 300 ml autoclave, equipped with a stirrer and temperature control, was flushed with nitrogen gas. Eight grams of one of the catalysts manufactured in Examples 18, 25 grams of monoethanol amine, 3.5 grams of water, and 65 grams of liquid ammonia were charged into the autoclave. The autoclave was closed, and hydrogen gas was introduced to a pressure of 5.5 MPa. The contents of the autoclave were heated to 200° C. and kept at this temperature with continuous stirring until the completion of the test.

Samples were withdrawn from the autoclave during the reaction and analyzed using Gas-Liquid Chromatography. The conversion percent of the compound charged for amination was calculated, as well as the weight percents of products formed in the reaction. The results obtained are reported in TABLE III.

EXAMPLE 20

A mixture of 6.25 grams of diethanolamine and 18.75 grams of monoethanolamine was reacted with ammonia as described in Example 19. The catalyst used was catalyst A1 described in Example 18, and as a comparison catalyst B1 was used. The results obtained are reported TABLE IV.

EXAMPLE 21

A mixture of 6.25 grams of aminoethyl ethanolamine and 18.75 grams of monoethanolamine was reacted with ammonia in the same manner as in Example 20. The results obtained are reported in TABLE IV.

EXAMPLE 22

A mixture of 12.5 grams of monoethylene glycol and 12.5 grams of monoethanolamine was reacted with ammonia in the same manner as in Example 20. The results obtained are reported in TABLE IV.

From the results shown in TABLE III and TABLE IV it is evident that the catalysts in accordance with the invention favor the formation of primary amino groups, and reduce the formation of cyclic compound, e.g. PIP, AEP and HEP.

The present disclosure relates to the subject matter disclosed in Swedish Application Ser. No. 8,304,828.-0, filed Sept. 9th, 1983, and Swedish Application Ser. No. 86,03088-9, filed July 11th, 1986, the entire specifications of which are incorporated herein by reference.

It will be understood that the above description of the present invention is susceptible to various modifications, changes and adaptations, and the same are intended to be comprehended within the meaning and range of equivalents of the appended claims.

TABLE I

| Example No. | Conversion % | Products formed, weight % | | | | | | Amino groups mole % | | |
|---|---|---|---|---|---|---|---|---|---|---|
| | | EDA | PIP | DETA | AEP | AEEA | HEP | Primary | Secondary | Tertiary |
| 1 | 53.1 | 67.6 | 8.3 | 13.3 | 0.9 | 9.6 | 0.4 | 86 | 14 | 0.3 |
| 2 | 57.8 | 66.7 | 9.2 | 13.7 | 1.5 | 8.7 | 0.3 | 85 | 15 | 0.5 |
| 3 | 52.9 | 65.9 | 7.2 | 14.7 | 1.2 | 14.0 | 0.3 | 86 | 14 | 0.3 |
| 4 | 57.3 | 69.7 | 8.7 | 14.5 | 1.0 | 5.9 | 0.2 | 86 | 14 | 0.3 |
| 5 | 61.0 | 68.8 | 7.1 | 15.0 | 0.8 | 7.9 | 0.3 | 87 | 13 | 0.3 |
| 6 | 61.1 | 69.3 | 6.6 | 15.6 | 0.7 | 7.3 | 0.3 | 87 | 12 | 0.3 |
| Comp.A. | 59.0 | 64.5 | 14.5 | 14.2 | 1.8 | 4.6 | 0.6 | 82 | 18 | 0.6 |
| 7 | 56.8 | 62.2 | 5.4 | 17.1 | 0.5 | 14.5 | 0.3 | 85 | 15 | 0.2 |
| 8 | 55.1 | 68.9 | 6.4 | 15.7 | 0.8 | 7.7 | 0.4 | 87 | 13 | 0.3 |
| 9 | 57.7 | 65.2 | 10.8 | 14.2 | 1.2 | 8.1 | 0.3 | 84 | 16 | 0.4 |
| 10 | 5.49 | 66.3 | 7.2 | 14.7 | 1.1 | 10.0 | 0.4 | 86 | 14 | 0.4 |
| 11 | 59.1 | 64.7 | 6.7 | 15.3 | 0.9 | 11.9 | 0.3 | 85 | 14 | 0.3 |
| 12 | 47.0 | 68.8 | 7.5 | 10.4 | 1.1 | 11.2 | 0.2 | 87 | 13 | 0.3 |
| 13 | 48.6 | 78.1 | 4.6 | 5.0 | 0.4 | 11.3 | 0.3 | 91 | 9 | 0.2 |
| 14 | 51.9 | 74.9 | 8.3 | 6.9 | 0.9 | 8.6 | 0.4 | 88 | 11 | 0.3 |
| 15 | 54.0 | 63.3 | 5.6 | 14.6 | 0.7 | 15.3 | 0.5 | 85 | 14 | 0.3 |
| 16 | 58.6 | 66.0 | 6.5 | 16.4 | 0.6 | 10.2 | 0.3 | 86 | 14 | 0.2 |
| 17 | 54.5 | 66.4 | 8.0 | 16.5 | 0.6 | 8.1 | 0.4 | 86 | 14 | 0.3 |

TABLE II

| CATALYST No. | METAL NITRATE | | RUTHENIUM COMPOUND | |
|---|---|---|---|---|
| | Metal | amount (grams) | Compound | Ruthenium amount (grams) |
| A1 | nickel | 10 | ruthenium chloride hydrate | 0.5 |
| B1 | nickel | 10 | — | — |
| A2 | nickel | 7.5 | ruthenium chloride hydrate | 0.5 |
| | copper | 2.2 | | |
| | chromium | 0.3 | | |
| B2 | nickel | 7.5 | | |
| | copper | 2.2 | | |
| | chromium | 0.3 | — | — |
| A3 | cobalt | 10 | ruthenium chloride hydrate | 0.5 |
| B3 | cobalt | 10 | — | — |
| A4 | nickel | 4 | ruthenium chloride hydrate | 0.25 |
| | cobalt | 4 | | |
| | iron | 4 | | |
| A5 | nickel | 4 | ruthenium chloride hydrate | 0.5 |
| | cobalt | 4 | | |
| | iron | 4 | | |
| A6 | nickel | 4 | ruthenium chloride hydrate | 1.0 |
| | cobalt | 4 | | |
| | iron | 4 | | |
| B4 | nickel | 4 | | |
| | cobalt | 4 | | |
| | iron | 4 | — | — |
| B5 | nickel | 4 | ruthenium nitrate | 0.5 |
| | cobalt | 4 | | |
| | iron | 4 | | |
| B6 | nickel | 4 | ruthenium nitrate | 1.0 |
| | cobalt | 4 | | |
| | iron | 4 | | |
| A7 | nickel | 10 | ruthenium bromide | 0.5 |
| B7 | nickel | 10 | — | — |
| A8 | nickel | 10 | ruthenium potassium chloride | 0.5 |
| A9 | nickel | 10 | ruthenium nitrosyl chloride | 0.5 |
| A10 | nickel | 10 | ruthenium potassium nitrosyl chloride | 0.5 |
| A11 | nickel | 10 | ruthenium ammonium chloride | 0.5 |
| B11 | nickel | 10 | ruthenium ammonium nitrate | 0.5 |

TABLE III

| Catalyst | Conversion, % | Products formed, weight % | | | | | | Amino groups, mole % | | |
|---|---|---|---|---|---|---|---|---|---|---|
| | | EDA | DETA | AEEA | PIP | AEP | HEP | Primary | Secondary | Tertiary |
| A1 | 76 | 60.0 | 20.3 | 6.1 | 9.9 | 2.3 | 1.4 | 82 | 17 | 0.9 |
| B1 | 76 | 54.4 | 14.2 | 4.4 | 20.8 | 4.4 | 1.5 | 74 | 24 | 1.5 |
| A2 | 40 | 81 | 7.7 | 4.1 | 6.7 | 0.2 | 0.3 | 91 | 9 | 0.1 |
| B2 | 40 | 75 | 4.5 | 2.8 | 15.5 | 1.5 | 0.7 | 85 | 15 | 0.6 |
| A3 | 88 | 56 | 7.9 | 5.3 | 25.5 | 3.1 | 1.3 | 73 | 26 | 1 |
| B3 | 88 | 43 | 7.7 | 6.5 | 33.8 | 5.5 | 2.4 | 62 | 36 | 2 |
| A4 | 60 | 67 | 7.7 | 8.5 | 12.8 | 2.0 | 2.0 | 83 | 16 | 1 |
| A5 | 60 | 72 | 7.9 | 8.0 | 7.7 | 1.0 | 1.4 | 88 | 12 | 1 |
| A6 | 60 | 71 | 10.2 | 6.9 | 9.2 | 1.4 | 1.3 | 86 | 13 | 1 |
| B4 | 60 | 58 | 9.9 | 19.9 | 14.1 | 2.5 | 3.3 | 77 | 22 | 1 |
| B5 | 60 | 61 | 9.2 | 10.1 | 13.9 | 2.6 | 3.2 | 80 | 19 | 1 |
| B6 | 60 | 62 | 10.0 | 7.1 | 16.0 | 2.4 | 2.5 | 79 | 19 | 1 |
| A7 | 60 | 60 | 14.5 | 5.5 | 8.1 | 1.7 | 1.2 | 86 | 13 | 1 |
| B7 | 60 | 63 | 11.2 | 7.3 | 13.8 | 2.5 | 2.2 | 81 | 18 | 1 |
| A8 | 60 | 69 | 14.7 | 5.4 | 8.1 | 1.7 | 1.2 | 86 | 13 | 1 |
| A9 | 60 | 69 | 13.9 | 5.5 | 9.0 | 1.6 | 1.0 | 86 | 13 | 1 |
| A10 | 60 | 70 | 12.3 | 5.3 | 9.3 | 2.0 | 1.1 | 86 | 13 | 1 |
| A11 | 60 | 69 | 13.2 | 5.8 | 8.4 | 2.3 | 1.3 | 86 | 13 | 1 |
| B11 | 60 | 63 | 10.5 | 6.1 | 14.0 | 3.6 | 2.8 | 80 | 18 | 1 |

TABLE IV

| Ex. | Catalyst | Conversion, % | Composition of reaction mixture after completion of the reaction, weight % | | | | | | | | Amino Groups, mole % | | |
|---|---|---|---|---|---|---|---|---|---|---|---|---|---|
| | | | EDA | MEA | PIP | DETA | AEP | AEEA | HEP | DEA | Primary | Secondary | Tertiary |
| 20 | A1 | 70 | 55 | 24 | 7.6 | 4.9 | 0.8 | 2.9 | 0.7 | 4.3 | 88 | 12 | 1 |
| | B1 | 70 | 33 | 23 | 14.7 | 7.2 | 3.2 | 13.2 | 2.5 | 4.3 | 68 | 29 | 2 |
| 21 | A1 | 60 | 30 | 30 | 7.4 | 7.3 | 0.9 | 23.0 | 1.7 | 0.0 | 80 | 18 | 1 |
| | B1 | 60 | 27 | 30 | 14.9 | 6.6 | 3.2 | 16.0 | 2.8 | 0.0 | 68 | 29 | 3 |
| 22 | A1 | 50 | 26 | 25 | 2.6 | * | 2.8 | * | 0.6 | 0.1 | 89 | 9 | 3 |
| | B1 | 50 | 30 | 27 | 8.8 | * | 2.1 | * | 1.8 | 0.6 | 79 | 19 | 2 |

*Due to difficulties in analysis, this component was not determined.

What is claimed is:

1. A process for the preparation of a ruthenium-promoted, halogen-containing, nickel and/or cobalt catalyst, which catalyst contains, based on the total weight of the catalyst, from 4–40% by weight of at least one metal selected from nickel and cobalt, from 0.1–5% by weight of ruthenium and a porous metal oxide support, the process comprising:
   impregnating, in one or more steps, a porous metal oxide support with a solution or slurry of at least one metallic compound selected from a nickel compound and a cobalt compound; and a solution or slurry of ruthenium compound, the porous metal oxide support being comprised of at least 50% by weight of a material selected from activated alumina and activated silica;
   reducing, in one or more steps, the at least one metallic compound and the ruthenium compound to nickel and/or cobalt and ruthenium metal; and
   introducing halogen into the catalyst by adding a halide compound as a liquid, gas or in solution at any stage of the process.

2. The process according to claim 1, wherein halogen is introduced into the catalyst by treating the porous metal oxide support with the halide compound prior to impregnating the porous metal oxide support with the at least one metallic compound and the ruthenium compound.

3. The process according to claim 1, wherein the porous metal oxide support is impregnated with the at least one metallic compound, and the at least one metallic compound is reduced to provide a first catalyst intermediate and wherein halogen is introduced into the catalyst by treating the first catalyst intermediate with the halide compound prior to impregnating with the ruthenium compound.

4. The process according to claim 1, wherein reduction of the at least one metallic compound and the ruthenium compound provides a second catalyst intermediate and wherein halogen is introduced into the catalyst by treating the second catalyst intermediate with the halide compound.

5. The process according to claim 1, wherein the porous metal oxide support is impregnated with a mixture of the at least one metallic compound, the ruthenium compound, and the halide compound.

6. The process according to claim 1, wherein the halide compound is a ruthenium halide compound and is added as the ruthenium compound.

7. The process according to claim 1, wherein the halide compound is any halide compound except a ruthenium halide compound.

8. The process according to claim 1, wherein the halide compound is any halide compound except a nickel halide compound or a cobalt halide compound.

9. The process according to claim 8, wherein the halide compound is any halide compound except a ruthenium halide compound.

10. The process according to claim 1, wherein the ruthenium compound is selected from the group consisting of ruthenium nitrate and ruthenium nitrosyl nitrate.

11. The process according to claim 1, wherein the halide compound is hydrochloric acid.

12. A process for the preparation of a ruthenium-promoted, halogen-containing, nickel and/or cobalt catalyst, comprising:
   providing a porous metal oxide support comprised of at least 50% by weight of a material selected from activated alumina and activated silica;
   impregnating the porous metal oxide support with a solution or slurry of at least one of a nickel compound and a cobalt compound to provide a first catalyst intermediate containing from 4 to 40% by weight of the at least one metallic compound measured as metal and based on the total weight of the finished catalyst;
   decomposing the at least one metallic compound of the first catalyst intermediate into metals or oxides under conditions of temperature and pressure effective to cause such decomposition and to provide a second catalyst intermediate containing one or more of at least one metal selected from nickel and cobalt, and at least one metal oxide selected from nickel oxide and cobalt oxide;
   impregnating the second catalyst intermediate with a solution or slurry of a ruthenium compound to provide a third catalyst intermediate containing from 0.1 to 5% by weight ruthenium measured as metal and based on the total weight of the finished catalyst;
   reducing the ruthenium compound of the third catalyst intermediate into ruthenium metal by causing the ruthenium compound to react with hydrogen gas at an elevated temperature sufficient to reduce the ruthenium compound to ruthenium metal;
   reducing the at least one metal oxide selected from nickel oxide and cobalt oxide to metal by causing the at least one metal oxide to react with hydrogen gas at an elevated temperature sufficient to reduce the at least one metal oxide to at least one metal selected from nickel and cobalt; and
   introducing halogen into the catalyst by adding a halide compound as a liquid, gas or in solution at any stage of the process so that the catalyst contains from 0.1 to 5 weight percent elemental halogen, based on the total weight of the finished catalyst.

13. The process according to claim 12, wherein halogen is introduced into the catalyst by treating the porous metal oxide support with the halide compound prior to any impregnating step.

14. The process according to claim 12, wherein halogen is introduced into the catalyst by preparing a mixture comprised of the halide compound and the at least one metallic compound and impregnating the porous metal oxide support with the mixture.

15. The process according to claim 12, wherein halogen is introduced into the catalyst in the decomposing step by decomposing the at least one metallic compound of the first catalyst intermediate in an atmosphere containing the halide compound.

16. The process according to claim 12, wherein halogen is introduced into the catalyst by treating the second catalyst intermediate with the halide compound prior to impregnating the second catalyst intermediate with a ruthenium compound.

17. The process according to claim 12, wherein halogen is introduced into the catalyst by providing a mixture comprised of the halide compound and a ruthenium compound and impregnating the second catalyst intermediate with the mixture.

18. The process according to claim 12, wherein halogen is introduced into the catalyst after the ruthenium compound is reduced to ruthenium metal, but prior to reducing to metal the at least one metal oxide selected from nickel oxide and cobalt oxide.

19. The process according to claim 12, wherein the halide compound is a volatile halide compound and wherein halogen is introduced into the catalyst by mixing the volatile halide compound with the hydrogen gas employed during one or more reduction step.

20. The process according to claim 12, wherein the halide compound is a ruthenium halide compound and is added as the ruthenium compound.

21. The process according to claim 12, wherein the halide compound is any halide compound except a ruthenium halide compound.

22. The process according to claim 12, wherein the halide compound is any halide compound except a nickel halide compound or a cobalt halide compound.

23. The process according to claim 12, wherein the ruthenium compound is selected from the group consisting of ruthenium nitrate and ruthenium nitrosyl nitrate.

24. The process according to claim 12, wherein the halide compound is hydrochloric acid.

25. A process for the preparation of a ruthenium-promoted, halogen-containing, nickel and/or cobalt catalyst comprising:
providing a porous metal oxide support comprised of at least 50% by weight of a material selected from activated alumina and activated silica;
impregnating the porous metal oxide support with a solution or slurry of at least one metallic compound selected from a nickel compound and a cobalt compound, and a solution or slurry of ruthenium compound to provide a catalyst intermediate containing, based on the total weight of the finished catalyst and measured as metal, from 4 to 40% by weight nickel and/or cobalt and from 0.1 to 5% by weight ruthenium;
reducing the at least one metallic compound and the ruthenium compound of the catalyst intermediate to metal by causing the at least one metallic compound and the ruthenium compound to react with hydrogen gas at an elevated temperature sufficient to reduce the at least one metallic compound and the ruthenium compound to the respective metals; and
introducing halogen into the catalyst by adding a halide compound as a liquid, gas or in solution at any stage of the process so that the catalyst contains from 0.1 to 5 weight % elemental halogen based on the total weight of the finished catalyst.

26. The process according to claim 25, wherein halogen is introduced into the catalyst by treating the porous metal oxide support with the halide compound prior to the impregnating step.

27. The process according to claim 25, wherein halogen is introduced into the catalyst during the impregnating step by providing a mixture comprised of the halide compound, the at least one metallic compound, and the ruthenium compound and by impregnating the porous metal oxide support with the mixture.

28. The process according to claim 25, wherein the halide compound is a volatile halide compound and wherein halogen is introduced into the catalyst during the reduction step by adding the volatile halide compound to the hydrogen gas employed during the reduction step.

29. The process according to claim 25, wherein the halide compound is a ruthenium halide compound and is added as the ruthenium compound.

30. The process according to claim 25, wherein the halide compound is any halide compound except a ruthenium halide compound.

31. The process according to claim 25, wherein the halide compound is any halide compound except a nickel halide compound or a cobalt halide compound.

32. The process according to claim 31, wherein the halide compound is any halide compound except a ruthenium halide compound.

33. The process according to claim 25, wherein the ruthenium compound is selected from the group consisting of ruthenium nitrate and ruthenium nitrosyl nitrate.

34. The process according to claim 25, wherein the halide compound is hydrochloric acid.

35. A ruthenium-promoted, halogen-containing, nickel and/or cobalt catalyst containing, based on the total weight of the catalyst, from 4 to 40% by weight of at least one metal selected from nickel and cobalt; from 0.1 to 5% by weight of ruthenium; from 0.1 to 5% by weight of halogen; and a porous metal oxide support comprised of at least 50% by weight of a material selected from activated alumina and activated silica, prepared by a process comprising:
impregnating the porous metal oxide support with a solution or slurry of at least one metallic compound selected from a nickel compound and a cobalt compound to provide a first catalyst intermediate;
decomposing the at least one metallic compound of the first catalyst intermediate into metals or oxides under conditions of temperature and pressure effective to cause such decomposition and to provide a second catalyst intermediate containing one or more of at least one metal selected from nickel and cobalt, and at least one metal oxide selected from nickel oxide and cobalt oxide;
impregnating the second catalyst intermediate with a solution or slurry of a ruthenium compound to provide a third catalyst intermediate;
reducing the ruthenium compound of the third catalyst intermediate into ruthenium metal by causing the ruthenium compound to react with hydrogen gas at an elevated temperature sufficient to reduce the ruthenium compound to ruthenium metal;

reducing the at least one metal oxide selected from nickel oxide and cobalt oxide to metal by causing the at least one metal oxide to react with hydrogen gas at an elevated temperature sufficient to reduce the at least one metal oxide to at least one metal selected from nickel and cobalt; and introducing halogen into the catalyst by adding a halide compound as a liquid, a gas or in solution at any stage of the process, wherein the halide compound is any halide compound except a ruthenium halide compound.

36. The ruthenium-promoted, halogen-containing, nickel and/or cobalt catalyst according to claim 35, wherein the halide compound is any halide compound except a nickel halide compound or a cobalt halide compound.

* * * * *